(12) United States Patent
Thramann

(10) Patent No.: US 7,862,589 B2
(45) Date of Patent: Jan. 4, 2011

(54) FACET REPLACEMENT

(75) Inventor: Jeffery Thramann, Longmont, CO (US)

(73) Assignee: Lanx, Inc., Broomfield, CO (US)

( * ) Notice: Subject to any disclaimer, the term of this patent is extended or adjusted under 35 U.S.C. 154(b) by 489 days.

(21) Appl. No.: 11/135,686

(22) Filed: May 24, 2005

(65) Prior Publication Data

US 2006/0271195 A1    Nov. 30, 2006

(51) Int. Cl.
*A61B 17/70* (2006.01)
*A61F 2/44* (2006.01)

(52) U.S. Cl. .................. 606/247; 623/17.11

(58) Field of Classification Search ... 623/17.11–17.16; 606/61
See application file for complete search history.

(56) References Cited

U.S. PATENT DOCUMENTS

| | | | | |
|---|---|---|---|---|
| 4,988,349 A | * | 1/1991 | Pennig | 606/58 |
| 5,360,430 A | * | 11/1994 | Lin | 606/61 |
| 5,540,688 A | * | 7/1996 | Navas | 606/61 |
| 5,755,796 A | * | 5/1998 | Ibo et al. | 623/17.16 |
| 5,961,516 A | * | 10/1999 | Graf | 606/61 |
| RE36,758 E | * | 6/2000 | Fitz | 623/17.11 |
| 6,267,764 B1 | * | 7/2001 | Elberg | 606/61 |
| 6,267,765 B1 | * | 7/2001 | Taylor et al. | 606/61 |
| 6,610,091 B1 | * | 8/2003 | Reiley | 623/17.11 |
| 6,811,567 B2 | * | 11/2004 | Reiley | 623/17.11 |
| 6,966,930 B2 | * | 11/2005 | Arnin et al. | 623/17.11 |
| 7,377,942 B2 | * | 5/2008 | Berry | 623/17.11 |
| 2005/0055096 A1 | | 3/2005 | Serhan et al. | |
| 2005/0080486 A1 | | 4/2005 | Fallin et al. | |
| 2005/0101954 A1 | | 5/2005 | Simonson | |
| 2005/0197700 A1 | | 9/2005 | Boehm et al. | |

OTHER PUBLICATIONS

Blain, "Vertebral Facet Joint Prosthesis and Method of Fixation" International Publication No. 2005/0177240 A1; International Publication Date Aug. 11, 2005.

* cited by examiner

*Primary Examiner*—Anu Ramana
(74) *Attorney, Agent, or Firm*—Holland & Hart LLP

(57) ABSTRACT

Facet replacement device is provided. The facet replacement device comprises a superior seating device coupled to a superior vertebral body and an inferior seating device coupled to an inferior vertebral body. The seating devices provide a joint to replace the facet. Another device comprises a superior vertebral body anchor with a first extension terminating in a joint connection, such as, a socket. An inferior vertebral body anchor has a second extension terminating in a corresponding joint connection, such as, a ball.

13 Claims, 4 Drawing Sheets

FACET REPLACEMENT

FIELD OF THE INVENTION

The present invention relates to surgical implants and, more particularly, to a facet replacement device.

BACKGROUND OF THE INVENTION

Referring to FIG. 1, a posterior, lateral perspective view of a vertebral segment 100 is shown. Vertebral segment 100 has facets 102, 104, 106, and 108. One or more of facets 102, 104, 106, and 108 on one or more vertebrae can become damaged, arthritic or the like. When this happens, a person experiences pain.

Currently, facet damage may be alleviated, in part, by fusing the superior and inferior vertebral bodies together. Fusing the segments together removes some of the pressure on the joint, which reduces the pain. Alternative non fusion technologies also exist, see for example, co-pending patent application Ser. No. 11/128,960 titled, spinal stabilization, and co-pending patent application Ser. No. 11/128,962 titled, pedicle screw spinal stabilization, both of which are incorporated herein by reference as if set out in full. These devices also attempt to reduce pain by removing some pressure on the facets. However, spinal stabilization is not a satisfactory solution to facet damage.

Some implants exist that attempt to build a bridge or the like over the joint. The bridge would remove, hopefully, all the pressure from the facet, which would remove the pain.

All the above solutions are not particularly satisfactory. Thus, it would be desirous to develop and improved facet replacement device.

SUMMARY OF THE INVENTION

To attain the advantages and in accordance with the purpose of the invention, as embodied and broadly described herein, a facet replacement device is provided. The facet replacement device comprises a superior seating device having a superior seating surface and a superior protrusion extending from the superior seating device opposite the superior seating surface that is coupled to a superior vertebral body. The device also comprises an inferior seating device having an inferior seating surface and an inferior protrusion extending from the inferior seating device opposite the inferior seating surface. The inferior protrusion is coupled to an inferior vertebral body. The superior seating surface and the inferior seating surface abut and form a joint.

The present invention also provides a facet replacement device comprising a superior anchor to couple to a superior pedicle and an inferior anchor to couple to an inferior pedicle. A first extension having a first end coupled to the superior anchor and a second end opposite the first end. A second extension having a third end coupled to the inferior anchor and a fourth end opposite the third end. The second end and the fourth end coupled to for a movable joint.

The foregoing and other features, utilities and advantages of the invention will be apparent from the following more particular description of a preferred embodiment of the invention as illustrated in the accompanying drawings.

BRIEF DESCRIPTION OF THE DRAWING

The accompanying drawings, which are incorporated in and constitute a part of this specification, illustrate embodiments of the present invention, and together with the description, serve to explain the principles thereof. Like items in the drawings are referred to using the same numerical reference.

DETAILED DESCRIPTION

Figure 1:
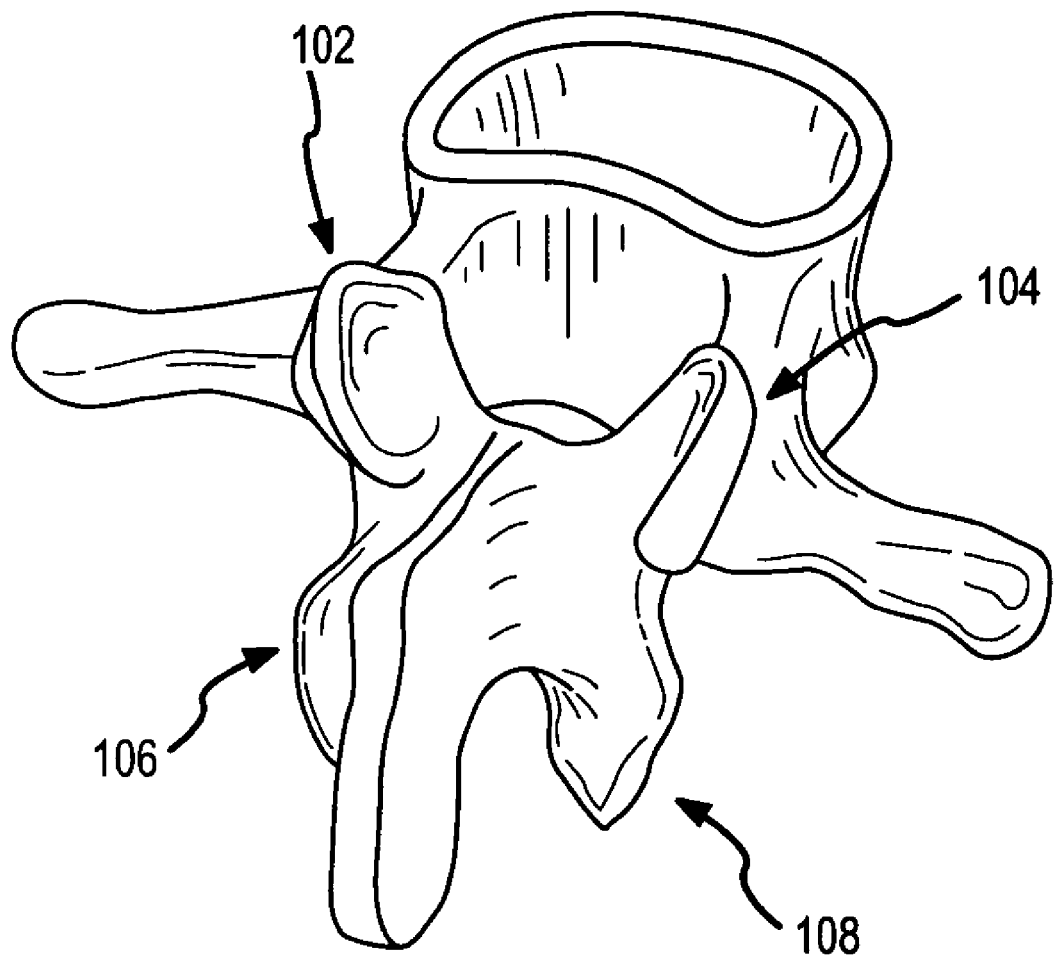
FIG. 1 is a posterior, lateral perspective view of a vertebrae.

The present invention will now be described with reference to FIGS. 1 to 6. The drawings are provided for illustration and should not be considered limiting or to scale. FIG. 1 shows an anterior, lateral perspective view of a vertebrae 100. Vertebrae 100 includes facets 102, 104, 106, and 108. One or more of facets 102, 104, 106, and 108 may become damaged, such as, for example, arthritic, causing pain.

Figure 2:
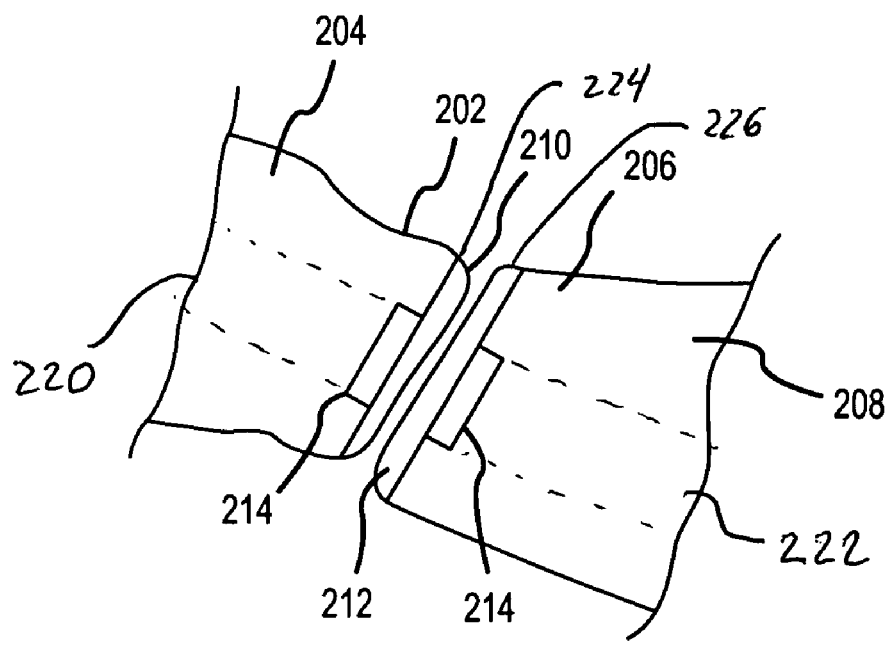
FIG. 2 is a cross-sectional view of a superior and an inferior facet with seating surface consistent with an embodiment of the present invention.

Referring now to FIG. 2, facet pain may be alleviated by replacing the facet surface. For example, FIG. 2 shows cross-sectional view of a superior facet 202 attached to a superior vertebral body 204, and an inferior facet 206 attached to an inferior vertebral body 208 (shown in part, and not to scale). Superior facet 202 has a superior seating device 210 with a seating surface 211 and inferior facet 206 has an inferior seating device 212 with an inferior seating surface 213. Superior seating device 210 and inferior seating device 212 can be of variable thicknesses depending on the amount of bone removal, if any, that is necessary. Superior seating device 210 and inferior seating device 212 are coupled to the respective facet using a protrusion 214, which will be explained further below but in general may be similar to a pin, screw, or the like. While a small gap is shown in the drawing for separation of the superior and inferior devices, it is understood that superior seating device 210 and inferior seating device 212 contact.

Instead of placing a pin in, for example, superior facet 202 to hold seating device 210, superior bone screw 220 and inferior bone screw 222 could be threaded through the facets. In this case, seating device 210 and seating device 212 would couple to the screws 220 and 222. Also, instead of using seating devices 210 and 212, seating devices 210 and 212 could be replaces with an articulating joint such as is described below with reference to FIGS. 5 and 6.

Superior seating device 210 and inferior seating device 212 would be formed of a biocompatible material, such as, for example, a titanium or titanium alloy, a shaped memory material, a polymer, or the like. Materials should be chosen that have a similar surface to surface friction to the facets that they are replacing. It is believed a metal surface on a metal surface would work well. Moreover, the material should be chosen to inhibit bone growth as bone growth could cause the joint to fuse. However, the superior bone/seating device interface 224 and inferior bone/seating device interface 226 should be constructed of a material to facilitate bone growth. Facilitating bone growth will assist with fusing the seating devices with the facets.

While it is believed adding both seatings would produce a good result, it is possible to only replace 1 facet surface. For example, if only inferior seating device 212 was used, superior seating device 210 would not be attached to superior facet 202. Thus, a bone to biocompatible joint would be formed.

Figure 3:
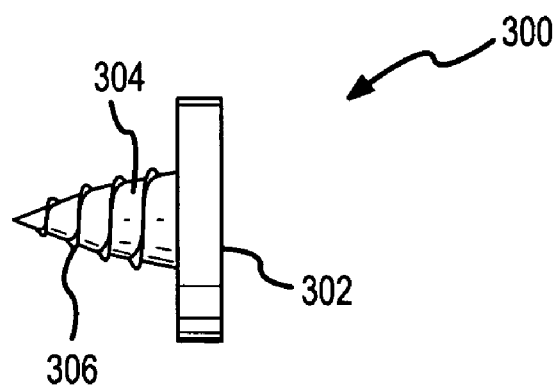
FIG. 3 shows the seating surface of FIG. 2 in more detail.

Referring now to FIG. 3, a seating device 300 is shown. Seating device 300 includes a seating surface 302 that abuts with a corresponding surface and/or bone to for a joint between superior and inferior vertebrae. Extending from seating device 300 opposite seating surface 302 is a protrusion 304. Protrusion 304 anchors seating device 300 to the vertebral body (not specifically shown in FIG. 3). Protrusion 304 could be any number of devices, such as, for example, a bone screw with threads 306 as shown. If protrusion 304 is a bone screw, threads 306 should be self taping.

Figure 4:
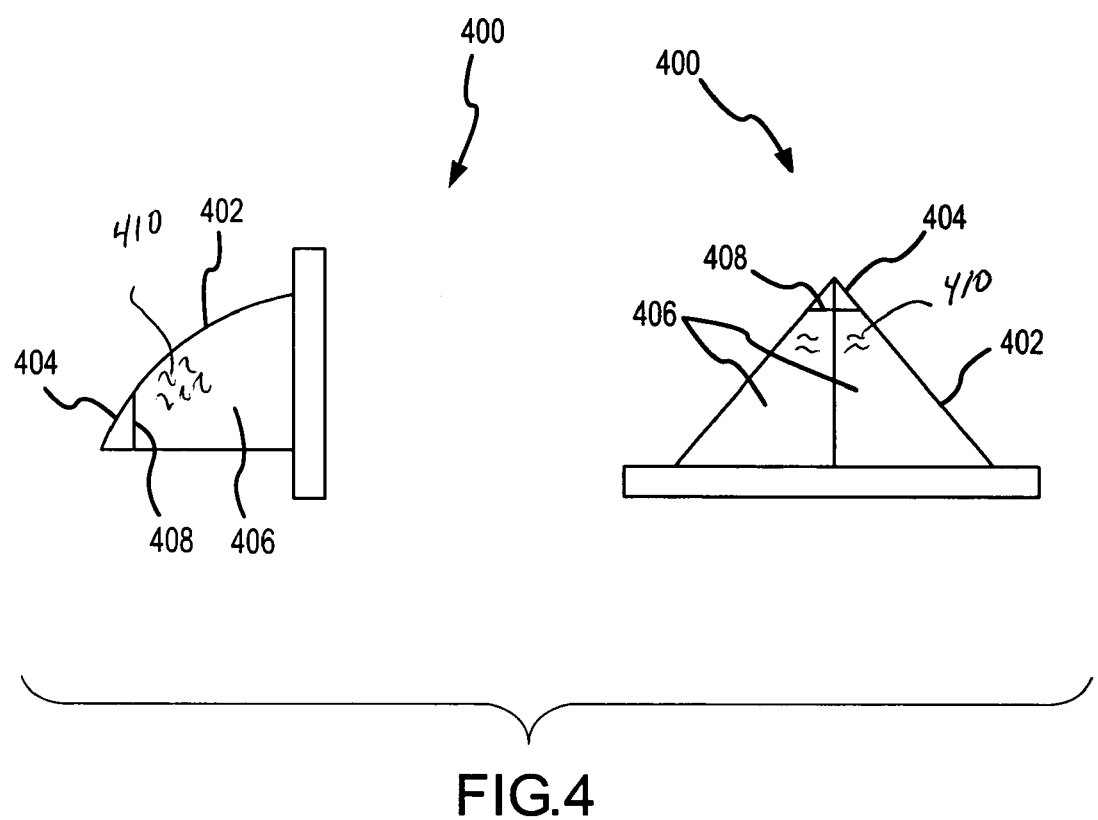
FIG. 4 shows an alternative construction of the seating surface of FIG. 2.

Referring now to FIG. 4, an alternative seating device 400 is shown. Seating device 400 is generally the same as seating device 300, but has a different shaped protrusion 402. Protrusion 402 in this case has a leading edge 404 that pieces the surface of the bone. Flanged sides 406 expand towards seating 400 to provide a frictional engagement with the bone. Flange sides 406 should have bone growth facilitating parts 410, such as, bone growth striations, beads, bone chips, or the like as is generally known in the art. Leading edge 404 may have a barb 408. Protrusion 302 could be a wedge shape, a keel, or the like. Protrusion 402 could, of course, be a straight cylindrical or square protrusion as desired.

Figure 5:
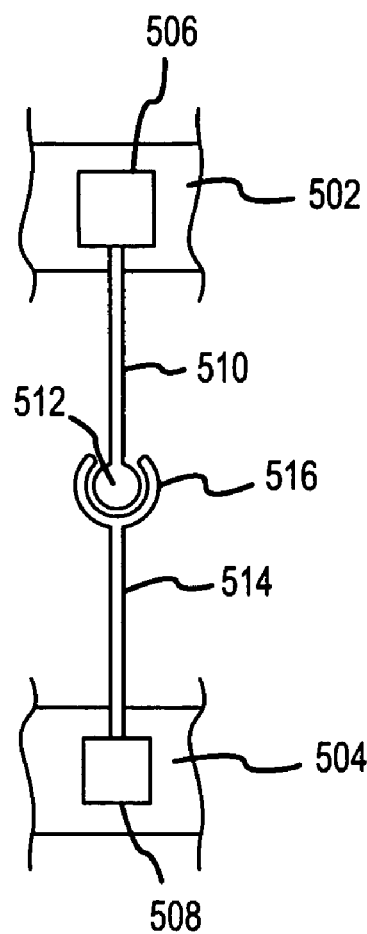
FIG. 5 shows another embodiment of a facet replacement device consistent with the present invention.
Figure 6:
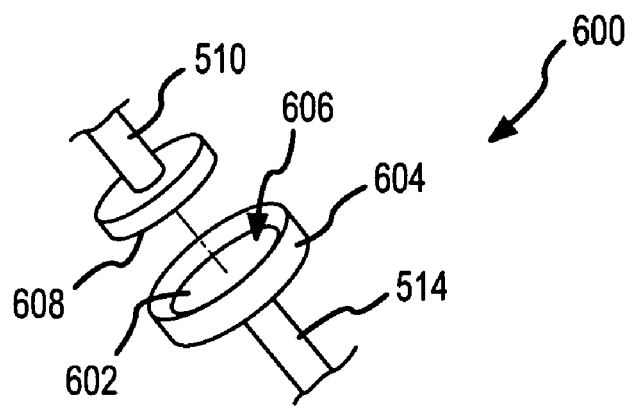
FIG. 6 shows an alternative joint for the replacement device of FIG. 5.

In some cases, the vertebral body may be sufficiently degraded or damaged that simply replacing the surface-to-surface contact joint is not sufficient. Referring to FIG. 5, another facet replacement device 500 is shown. FIG. 5 is not drawn to scale and is sufficiently exploded for reference. FIG. 500 shows a part of superior pedicle 502 and a part of an inferior pedicle 504. As can be appreciated, in this case the superior facet and inferior facet have been surgically removed. A superior pedicle screw and anchor 506, or the like, is attached to superior pedicle 502. A similar inferior pedicle screw and anchor 508, or the like, is attached to the inferior pedicle 504. A first extension 510 is attached to screw and anchor 506, which connection may be similar to a conventional rod attachment and is not further explained herein, extends towards inferior pedicle 504. First extension 510 is connected to screw and anchor 508 at one end and terminates in a joint connection 512 at a second end, which in this case is shown as a ball 512. A second extension 514 is attached to screw and anchor 508 and extends towards superior pedicle 502. Second extension 514 is connected to screw and anchor 510 at one end and terminates in a corresponding joint connection 516, which in this case is shown a socket 516. Socket 516 envelops ball 512 to provide a conventional ball and socket joint that permits relative movement between superior pedicle 502 and inferior pedicle 504. Notice, the ball and socket could be reversed or replaced with other joint connection. For example, the ball and socket joint could be replaced with a surface to surface joint 600, see FIG. 6. In this case, a first surface 602 would have an edge 604 forming a recess 606. A second surface 608 would fit in recess 606 to provide the surface to surface contact, but edge 604 would constrain the joint movement.

An embodiment of the present invention has been described with a degree of particularity. It should be understood that this description has been made by way of example, and that the invention is defined by the scope of the following claims.

We claim:

1. A facet joint replacement device for implantation below a patient's skin completely within the patient's body adjacent a vertebral joint comprised of a superior vertebra and an inferior vertebra, each vertebra having facets projecting posteriorly from the vertebral body, a facet of the superior vertebra and a facet of the inferior vertebra defining an articulating joint between them, the facet joint replacement device, comprising:

a superior joint component sized to replace an absent portion of a facet on a posterior portion of the superior vertebra, the superior joint component being sized to fit below the skin completely within the body adjacent the posterior portion of the superior vertebra, the superior joint component having a superior anchor, a first rod extension, and a first component of a joint connection, the first rod extension defining a first longitudinal axis between the superior anchor and the first component of the joint connection, the superior anchor configured to couple to the superior vertebra via an outwardly extending superior protrusion, the first rod extension having a first end coupled to the superior anchor and a second end having the first component of the joint connection opposite the first end, and the first rod extension having a distinct portion relative to the first component of the joint connection and extending a distance from the superior anchor to the first component of the joint connection;

an inferior joint component sized to replace an absent portion of a facet on a posterior portion of the inferior vertebra, the inferior joint component being sized to fit below the skin completely within the body adjacent the posterior portion of the inferior vertebra, the inferior joint component having an inferior anchor, a second rod extension, and a second component of the joint connection, the second rod extension defining a second longitudinal axis between the inferior anchor and the first component of the joint connection, the inferior anchor configured to couple to the inferior vertebra via an outwardly extending inferior protrusion, the second rod extension having a third end coupled to the inferior anchor and a fourth end having the second component of the joint connection opposite the third end, and the second rod extension having a distinct portion relative to the second component of the joint connection and extending a distance from the inferior anchor to the second component of the joint connection; wherein the first component of the joint connection at the second end and the second component of the joint connection at the fourth end form a movable joint permitting articulation between the superior and inferior vertebrae;

wherein, in at least one position, the first longitudinal axis of the superior joint component and the second longitudinal axis of the inferior joint component are selectively positionable to align coaxially with respect to one another; and wherein the first component of the joint connection at the second end is a ball and the second component of the joint connection at the fourth end is a socket forming a ball and socket joint.

2. The device of claim 1 wherein the superior protrusion is threaded to thread into the superior vertebral body and the inferior protrusion is threaded into the inferior vertebral body.

3. The device of claim 1 wherein the superior protrusion is self tapping and the inferior protrusion is self tapping.

4. The device of claim 1 wherein the superior protrusion is a pin and the inferior protrusion is a pin.

5. The device of claim 4 wherein the pin has a leading edge.

6. The device of claim 5 wherein the pin has flanged sidewalls.

7. The device of claim 5 wherein the pin has a barb.

8. The device of claim 5 herein the pin is keel shaped.

9. The device of claim 1 wherein the second end and the fourth end comprise a biocompatible metal and form a metal-on-metal movable joint.

10. The device of claim 9 wherein the biocompatible metal is a shape memory alloy.

11. The device of claim 1, wherein the superior protrusion, first end, second end, third end, fourth end, and inferior protrusion are generally collinear when the device is implanted in the human spine.

12. A facet joint replacement device for implantation below a patient's skin completely within the patient's body adjacent a vertebral joint comprised of a superior vertebra and an inferior vertebra, each vertebra having facets projecting posteriorly from the vertebral body, a facet of the superior vertebra and a facet of the inferior vertebra defining an articulating joint between them, the facet joint replacement device, comprising:

a superior joint component sized to replace an absent portion of a facet on a posterior portion of the superior vertebra, the superior joint component being sized to fit below the skin completely within the body adjacent the posterior portion of the superior vertebra, the superior joint component having a superior anchor, a first rod extension, and a first component of a joint connection, the first rod extension defining a first longitudinal axis between the superior anchor and the first component of the joint connection, the superior anchor configured to couple to the superior vertebra via an outwardly extending superior protrusion, the first rod extension having a first end coupled to the superior anchor and a second end having the first component of the joint connection opposite the first end, and the first rod extension having a distinct portion relative to the first component of the joint connection and extending a distance from the superior anchor to the first component of the joint connection;

an inferior joint component sized to replace an absent portion of a facet on a posterior portion of the inferior vertebra, the inferior joint component being sized to fit below the skin completely within the body adjacent the posterior portion of the inferior vertebra, the inferior joint component having an inferior anchor, a second rod extension, and a second component of the joint connection, the first rod extension defining a first longitudinal axis between the superior anchor and the first component of the joint connection, the inferior anchor configured to couple to the inferior vertebra via an outwardly extending inferior protrusion, the second rod extension having a third end coupled to the inferior anchor and a fourth end having the second component of the joint connection opposite the third end, and the second rod extension having a distinct portion relative to the second component of the joint connection and extending a distance from the inferior anchor to the second component of the joint connection; wherein the first component of the joint connection at the second end and the second component of the joint connection at the fourth end form a movable joint permitting articulation between the superior and inferior vertebrae;

wherein, in at least one position, the first longitudinal axis of the superior joint component and the second longitudinal axis of the inferior joint component are selectively positionable to align coaxially with respect to one another; and wherein the first component of the joint connection at the second end is a socket and the second component of the joint connection at the fourth end is a ball forming a ball and socket joint.

13. The device of claim 12, wherein the superior protrusion, first end, second end, third end, fourth end, and inferior protrusion are generally collinear when the device is implanted in the human spine.

* * * * *